United States Patent
Silver et al.

(10) Patent No.: US 12,193,898 B1
(45) Date of Patent: Jan. 14, 2025

(54) UNCURED PONTIC MATERIAL FOR ORTHODONTIC CLEAR ALIGNERS OR RETAINERS

(71) Applicant: OrVance, LLC, Caledonia, MI (US)

(72) Inventors: Michael Edward Silver, Lake City, MI (US); Ronald J. Schutt, Ludington, MI (US)

(73) Assignee: OrVance, LLC, Caledonia, MI (US)

(*) Notice: Subject to any disclaimer, the term of this patent is extended or adjusted under 35 U.S.C. 154(b) by 0 days.

(21) Appl. No.: 17/196,614

(22) Filed: Mar. 9, 2021

Related U.S. Application Data

(60) Provisional application No. 62/987,006, filed on Mar. 9, 2020.

(51) Int. Cl.
*A61C 13/00* (2006.01)
*A61C 7/08* (2006.01)
(Continued)

(52) U.S. Cl.
CPC ............ *A61C 13/0022* (2013.01); *A61C 7/08* (2013.01); *A61C 13/082* (2013.01); *A61K 6/78* (2020.01);
(Continued)

(58) Field of Classification Search
CPC ..... A61C 5/20; A61C 13/082; A61C 13/0022; A61K 6/896
(Continued)

(56) References Cited

U.S. PATENT DOCUMENTS

| | | |
|---|---|---|
| 3,455,872 A | 7/1969 | Nelson |
| 4,497,926 A | 2/1985 | Toy |

(Continued)

FOREIGN PATENT DOCUMENTS

| | | |
|---|---|---|
| CA | 2858830 A1 | 6/2013 |
| EP | 2544651 A1 | 1/2013 |

(Continued)

OTHER PUBLICATIONS

NuSil Premium and Class VI Product Guide. Product guide [online]. Avantor, Jan. 2019 [retrieved on Jul. 13, 2023]. Retrieved from the Internet: <URL: http://www.scientiasc.com.br/site-novo/pdf19/silicone-uso-medico/nusil-premium-care-product-guide-2019.pdf> (Year: 2019).*

(Continued)

*Primary Examiner* — Cris L. Rodriguez
*Assistant Examiner* — Courtney N Huynh
(74) *Attorney, Agent, or Firm* — Nyemaster Goode P.C.

(57) ABSTRACT

The present disclosure is generally directed toward a pontic material that is pliable and easily moldable, possesses a higher tear resistance to resist fragmenting and thus is long lasting, can be pigmented to achieve a good color match to adjacent teeth, and be fashioned into a pontic by the patient at home so as to free the orthodontist and their staff from having to do this purely aesthetic and time-consuming procedure. In addition, the pontic material of the present disclosure is typically permanently pliable so that an untrained person such as a patient would have unlimited time to make corrections to the shape of the material to obtain an aesthetically pleasing shape and typically do so without the use of tools or any specialized tools or equipment.

20 Claims, 4 Drawing Sheets

(51) Int. Cl.
  *A61C 13/08* (2006.01)
  *A61K 6/78* (2020.01)
  *A61K 6/896* (2020.01)
(52) U.S. Cl.
  CPC ........ *A61K 6/896* (2020.01); *A61C 2201/002* (2013.01)
(58) Field of Classification Search
  USPC .............................................. 433/6; 523/109
  See application file for complete search history.

(56) References Cited

U.S. PATENT DOCUMENTS

| | | | |
|---|---|---|---|
| 4,503,116 A | | 3/1985 | Lapidus |
| 4,529,748 A | | 7/1985 | Wienecke |
| 4,801,475 A | | 1/1989 | Halpern et al. |
| 4,957,783 A | | 9/1990 | Gabryszewski |
| 5,310,563 A | * | 5/1994 | Curtis .................... A61K 8/891 106/35 |
| 5,624,745 A | | 4/1997 | Lapidus |
| 5,700,478 A | | 12/1997 | Biegajski et al. |
| 5,938,435 A | | 8/1999 | Raspino, Jr. |
| 6,447,290 B1 | | 9/2002 | Williams |
| 6,638,881 B2 | | 10/2003 | Lapidus |
| 7,195,484 B1 | | 3/2007 | Wagner |
| 7,312,256 B2 | | 12/2007 | Borja |
| 7,789,662 B2 | | 9/2010 | Van Eikeren et al. |
| 8,007,277 B2 | | 8/2011 | Fischer et al. |
| 8,936,026 B2 | | 1/2015 | Hannapel et al. |
| 9,375,292 B2 | | 6/2016 | Peuker et al. |
| 9,987,102 B2 | | 6/2018 | Hannapel et al. |
| 9,987,103 B1 | | 6/2018 | Hannapel et al. |
| 10,391,040 B1 | * | 8/2019 | Schutt ...................... A61K 8/19 |
| 11,083,544 B1 | * | 8/2021 | Silver ...................... C08J 7/056 |
| 11,607,371 B1 | * | 3/2023 | Silver .................. B65D 75/367 |
| 11,622,834 B1 | * | 4/2023 | Silver ...................... A61C 5/70 523/115 |
| 2003/0138715 A1 | * | 7/2003 | Barthel .................. C01B 33/18 430/108.7 |
| 2003/0205234 A1 | | 11/2003 | Bardach et al. |
| 2004/0202983 A1 | * | 10/2004 | Tricca ...................... A61C 7/00 433/215 |
| 2005/0089820 A1 | | 4/2005 | Allred et al. |
| 2005/0181324 A1 | | 8/2005 | Hare |
| 2005/0215668 A1 | * | 9/2005 | Scholz ...................... C08K 9/04 524/493 |
| 2005/0239015 A1 | | 10/2005 | Dragan |
| 2006/0063128 A1 | | 3/2006 | Dragan |
| 2007/0015107 A1 | | 1/2007 | Mannschedel et al. |
| 2007/0185237 A1 | | 8/2007 | Rajaiah et al. |
| 2008/0085493 A1 | * | 4/2008 | Sun .................... A61C 13/0003 433/223 |
| 2008/0293015 A1 | | 11/2008 | Wong et al. |
| 2009/0087809 A1 | | 4/2009 | Jessop et al. |
| 2011/0315151 A1 | | 12/2011 | Schabert |
| 2012/0107768 A1 | | 5/2012 | Diedwardo |
| 2012/0199138 A1 | | 8/2012 | Hannapel et al. |
| 2014/0017637 A1 | | 1/2014 | Cinader, Jr. et al. |
| 2014/0287175 A1 | * | 9/2014 | Krawiec .................. H01B 3/46 428/447 |
| 2015/0037266 A1 | | 2/2015 | Boyd et al. |
| 2015/0209120 A1 | * | 7/2015 | Hannapel ................ A61C 7/125 427/2.29 |
| 2015/0297550 A1 | | 10/2015 | Jay |
| 2015/0368440 A1 | * | 12/2015 | Scholz .................... C07F 7/188 524/266 |
| 2023/0248477 A1 | * | 8/2023 | Silver ...................... A61K 6/60 606/76 |

FOREIGN PATENT DOCUMENTS

| | | | | |
|---|---|---|---|---|
| EP | 2698171 A1 | * | 2/2014 | .............. A61L 2/07 |
| WO | 2011112193 A1 | | 9/2011 | |
| WO | 2012109174 A2 | | 8/2012 | |
| WO | WO-2013130552 A1 | * | 9/2013 | .......... A61C 13/082 |

OTHER PUBLICATIONS

NuSil MED-4174 Silicone, One Part High Consistent Elastomer—Restricted Medical Use, MatWeb, www.matweb.com/search/datasheettext.aspx?matguid=4e4cdf84847c4806bc411e66e9416a7f. (Year 2020).
Dow Corning, "SILASTIC BioMedical Grade ETR Elastomers (Q7-4535, Q7-4550, Q7-4565), " Product Information, Ref. No. 51-0602C-01, Sep. 9, 2005, 6 pages.
Wacker, "ELASTOSIL R plus 4305/80 High Consistency Silicone Rubber (HCR)," Apr. 4, 2023, 3 pages.
Wacker, "ELASTOSIL R plus 4305/60 S High Consistency Silicone Rubber (HCR)," Apr. 4, 2023, 3 pages.
Wacker, "ELASTOSIL R plus 4000/50 High Consistency Silicone Rubber (HCR)," Oct. 11, 2022, 3 pages.
Wacker, "ELASTOSIL R 401/80 S High Consistency Silicone Rubber (HCR)," Mar. 16, 2023, 4 pages.
Wacker, "ELASTOSIL R 401/50 S High Consistency Silicone Rubber (HCR)," Mar. 16, 2023, 4 pages.
Avantor, "MED-4174 High sonsistency silicone elastomer," Biomaterials Premium Care Line, Rev. B, Nov. 26, 2018, 3 pages.
Avantor, "MED-4174 High sonsistency silicone elastomer," Biomaterials Premium Care Line, Rev. C, Nov. 16, 2018, 3 pages.
Hoshine, "Stock Code 603260.SH," Apr. 2020, 8 pages.

* cited by examiner

UNCURED PONTIC MATERIAL FOR ORTHODONTIC CLEAR ALIGNERS OR RETAINERS

CROSS-REFERENCE TO RELATED APPLICATION

This application claims priority to U.S. Provisional Application Ser. No. 62/987,006, filed on Mar. 9, 2020, entitled "UNCURED PONTIC MATERIAL FOR ORTHODONTIC CLEAR ALIGNERS OR RETAINERS," the disclosure of which is hereby incorporated herein by reference in its entirety.

BACKGROUND

Orthodontic plastic clear aligners are widely used to assist in the straightening or realignment of teeth. The primary advantage they offer over traditional orthodontic brackets and systems is that they are much less visible and thus yield an aesthetic benefit during the treatment period. Clear aligners have thus become an increasingly popular alternative to traditional braces. The aligner trays are made with a strong plastic material that typically is fabricated to fit the patient's teeth. As treatment progresses, the patient switches aligners during different stages of the process. Each aligner tray is a little different, causing the teeth to move a little more with every tray change. Each set of aligners is worn for a week or two before going to the next set. Over time, teeth reach their ideal position, according to the orthodontist's plan. Aligners are worn for at least 20 hours each day. The total number of aligners will vary by the needs of each patient. Most patients go through 20 to 30 trays during the treatment period.

A common issue that arises for patients in aligner treatment is the loss of a tooth. Such loss can be due to purposeful extraction to provide room for the other teeth to move, or from an accidental impact to the mouth. Another common issue is the chipping of a tooth due to accidental impact to the mouth or the chewing of a hard substance during eating (aligner trays are typically removed and not worn during eating). A missing or chipped tooth that is visible is aesthetically unpleasing and would be of particular concern to aligner patients, who generally choose such treatment in the first place for its aesthetic advantages over traditional braces. Orthodontists accommodate these patients by fabricating a pontic. In the fields of dentistry and orthodontia, traditionally a pontic has referred to an artificial tooth on a dental bridge, but this term is often used now to refer to any artificial tooth that replaces a missing natural tooth. For patients with a missing or chipped tooth in aligner treatment, an orthodontist or a trained member of their staff might fabricate a pontic that inserts into and is held into the space of a clear aligner where the missing natural tooth would have been.

Historically, a pontic is often made of a hard resin material that is shaped to fit the void via an initial cast of the teeth, followed by creating a lingual groove in the pontic, adjusting the pontic to get it to fit into the cast model, using a gel to stabilize the pontic in the model, lubricating the model with mold release, and thermoforming a plastic resin over the model to fabricate the aligner to arrive at an aligner with the pontic held into the aligner. Once an orthodontist or staff member is involved making a pontic, it is expensive, even before material costs are added. Materials make up less than 6% of office overhead, whereas personnel cost is at least twice that and diverts professionals away from treatment to aesthetics. Additionally, when used in connection with aligners, pontics need to be fabricated for many of the aligners employed during the treatment period.

Another method of producing aligner pontics uses "pontic paint" which involves the painting on of multiple coats of the material onto the aligner. Each coat of "pontic paint" must be cured. This can involve subjecting the "pontic paint" material to heat or UV light. Achieving an aesthetic result requires an experienced professional and is non-forgiving of mistakes during application due to the fact that each layer must be cured and is thereafter essentially unalterable without damage occurring to the cured "pontic paint".

Yet another method makes use of a two-part viscous polyvinylsiloxane material that cures to a solid rubber shortly after mixing the two parts. Inadequate mixing, improper placing, or improper shaping during the cure period can lead to an unpleasing (aesthetically) result, or a pontic that does not stay in place, and like the other methods is best accomplished by a professional. In all of these cases, the material used to fashion a pontic is ultimately non-pliable and cannot be easily or at all reshaped.

Recently pontic wax has been advertised. These products are essentially the intraoral dental wax used for relief from irritation due to orthodontic appliances that is made more opaque, and in some cases, more yellow than traditional intraoral dental wax, which is naturally opaque. It is important to point out that patient's teeth come in many shades. When fashioning pontics as described above, an orthodontist will color match the resin or curable material to a patient's tooth using the VITA Classical Shade Guide well known to orthodontists and dentists (the resin pontics, paints, and other curable materials are available in these VITA shades). To most aligner patients needing a pontic, a good color match to the adjacent teeth is critically important. Unfortunately, pontic wax is often a poor color match, and it also suffers the known shortcomings of dental wax which includes poor pliability and hardness, making it difficult to shape, and having a low tear resistance and thus a tendency to fragment.

SUMMARY

The pontic material of the present disclosure is pliable and easily moldable, possesses a higher tear resistance to resist fragmenting and thus is long lasting, can be pigmented to achieve a good color match to adjacent teeth, and be fashioned into a pontic by the patient at home so as to free the orthodontist and their staff from having to do this purely aesthetic and time-consuming procedure. In addition, the pontic material of the present disclosure is typically permanently pliable (remains permanently uncured if a curable material due to purposeful absence of a curing catalyst such as platinum or peroxides) so that an untrained person such as a patient would have unlimited time to make corrections to the shape of the material to obtain an aesthetically pleasing shape and typically do so without the need for tools or any specialized tools or equipment. The pontic material of the present disclosure typically allows for automatic shaping against the irregular gum line or the jagged edge of a chipped tooth by simply placing the material into the appropriate aligner or retainer position and then placing the aligner or retainer onto the teeth such that the irregular gum line or broken tooth edge presses against and shapes the pontic material. The pontic material of the present disclosure further also typically allows patients who do not visit an orthodontist during treatment due to use of so called "direct"

or "mail-order" aligners to fashion pontics themselves as needed. Each of these features are seen as very beneficial and desirable for orthodontic professionals and their patients.

An aspect of the present disclosure includes a composition configured for use in a plastic orthodontic aligner tray or dental retainer and configured to act as a pontic via placement of the composition into the aligner or dental retainer tray and shaping while in the aligner or dental retainer with or without the aid of a tool. The composition/pontic material of the present disclosure typically includes an admixed homogeneous composite having an uncured, uncrosslinked high consistency rubber base, more typically a silicone, uncrosslinked high consistency rubber base; and one or more metal oxide pigments.

DETAILED DESCRIPTION OF EMBODIMENTS

Figure 1:
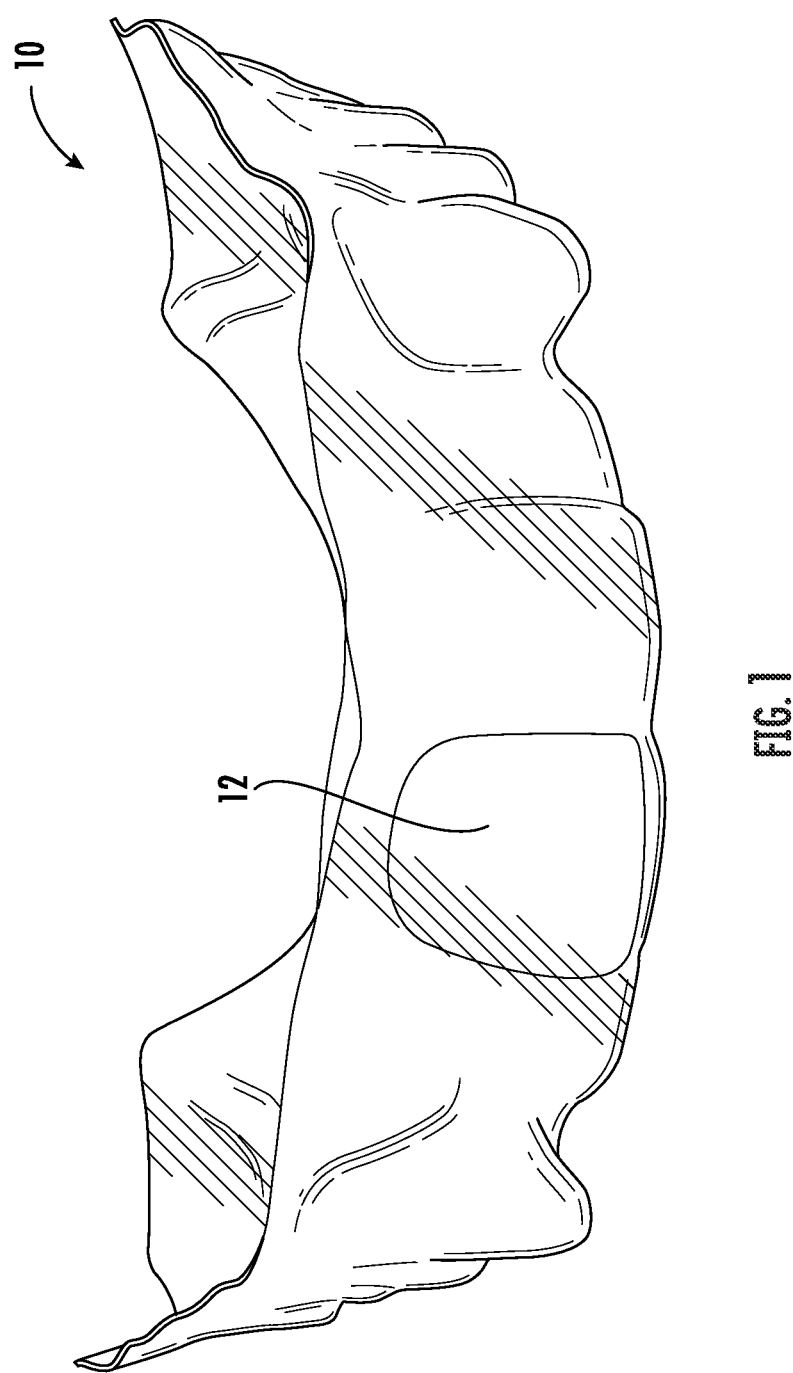
FIG. 1 is an elevated front perspective view of a clear plastic aligner tray according to an aspect of the present disclosure.
Figure 2:
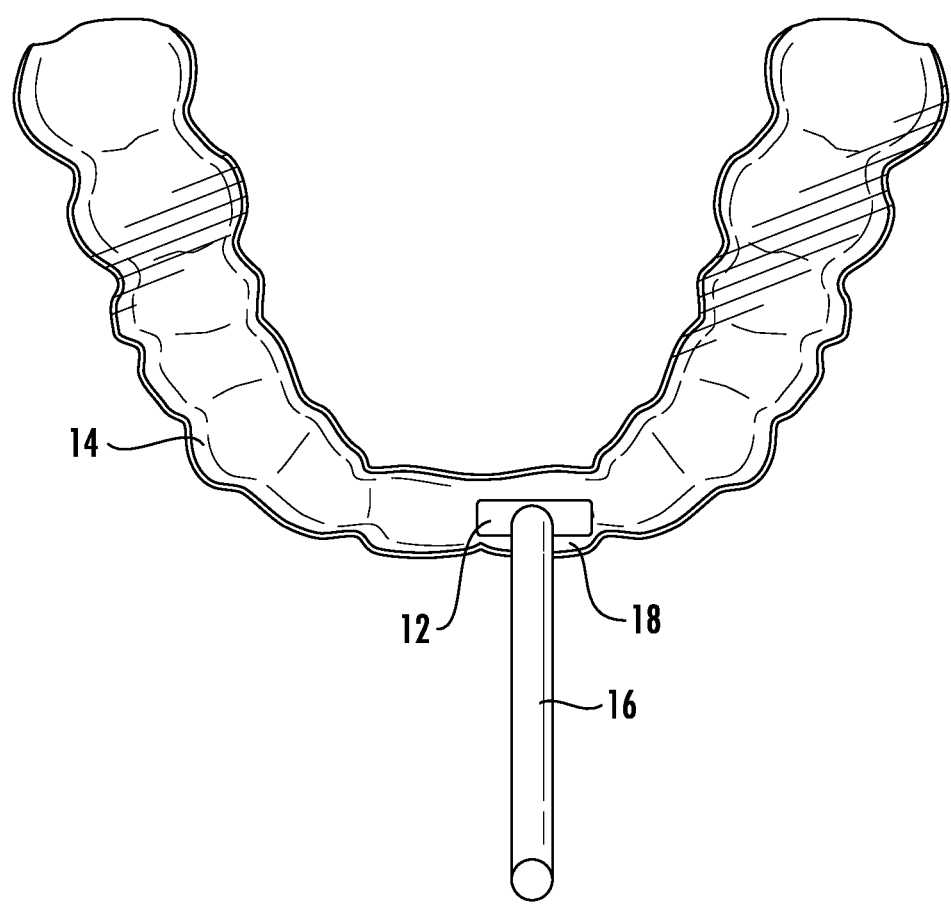
FIG. 2 is an inside perspective view of the shaped inventive pontic material in a clear plastic aligner tray.

Before the subject matter of the present disclosure is described further, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting, instead, the scope of the present disclosure will be established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

In this specification and the appended claims, the singular forms "a," "an" and "the" include plural reference unless the context clearly dictates otherwise.

The pontics compositions and methods of the present disclosure may comprise, consist of, or consist essentially of the elements of the products as described herein, as well as any additional or optional element described herein or otherwise useful in pontic applications. consists essentially of or consisting essentially of mean that the steps, composition or formulation (a) necessarily includes the listed ingredients and (b) is open to unlisted ingredients that do not materially affect the basic and novel properties of the composition. For example, in this case, while potential some amount of cross-linking catalyst could be added and not cross-link the uncured, uncrosslinked silicone high consistency rubber base; however, if an amount of cross-linking catalyst material is included in the pontic compositions of the present disclosure to substantially or completely cross-link or cure the pontic compositions they materially change the functioning of the composition because its shape is no longer permanently adjustable.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the Applicant intends to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

Also, as discussed herein tooth means a single tooth and teeth means more than one tooth, but the concepts of the present disclosure and the composites, systems and other disclosed materials of the present disclosure may apply to one or more teeth unless specifically indicated otherwise herein. Tooth is meant to encompass one or more teeth unless indicated otherwise.

As shown in general in FIGS. 1-4, the present disclosure is generally directed toward orthodontic plastic clear aligner trays and dental retainers, typically a human orthodontic plastic clear aligner 10 or dental retainer, and methods of using the devices in these trays. Patients receiving dental implants often need to wear a plastic retainer (similar in appearance to a plastic aligner) that prevents teeth from moving during the interval between tooth extraction and placement of the implant, and that a pontic is often fashioned for the retainer in a similar fashion as described herein for aligners to yield an aesthetically pleasing appearance during the aforementioned interval.

The retainers and aligners 10 of the present disclosure employ an uncured (uncrosslinked) silicone high consistency rubber base and one or more pigments acceptable for the buccal cavity, typically metal oxide pigments. The uncured (uncrosslinked) silicone high consistency rubber base employed is safe for the oral environment, more pliable than previous compositions, comfortable, and has superior tensile strength, typically the material of the present disclosure tolerates over 30 times more strain without breaking as compared to traditional orthodontic relief wax, based on tensile testing per ASTM D412 guidance. Additionally, the uncured (uncrosslinked) silicone high consistency rubber base employed is more than 18 times more pliable compared to traditional orthodontic relief wax, based on tensile testing per ASTM D412 guidance. Additionally, the uncured (uncrosslinked) silicone high consistency rubber base employed is more than 16 times more transmitting of visible light compared to traditional orthodontic relief wax, based on testing performed using a dual-beam Hitachi U-2910 UV-Vis spectrometer, making it a clearer base material for subsequent pigmentation to achieve desired tooth color(s).

As shown in the figures, the devices/compositions of the present disclosure are easily placed into an orthodontic clear plastic aligner 10 or dental retainer tray and may be molded in place within a clear aligner or dental retainer by a layperson (in situ) with just fingers or with fingers and a tool to achieve a tooth shaped facsimile (a pontic 12) and results in the appearance of a tooth at the position where a tooth is missing or a portion of the tooth that is missing from the tooth being chipped. Typically, the pontic is created on an internal surface 14 of the retainer or aligner 10 within a tooth packet 18. The devices/compositions are not cured, but are purposefully finger pliable without the use of tools and shaped with fingers and/or with the use of small implements such as a shaping stick 16, which can be made from wood, plastic or metal. The devices yield at least the following novel results:

(1) The devices are easily moldable and shapeable into a satisfactory tooth shape in situ within the aligner or retainer by both trained professional orthodontic staff and by untrained patients.

(2) The devices stay in place while the aligner or retainer is worn even though they may not entirely fill the void-of-tooth space in the aligner tray and are typically substantially free or free of any adhesive component.

(3) The devices of the present disclosure do not "cure". Unlike the case of the pontic materials of the present disclosure, light cured resins must be cured for about 10-30 seconds and the pontic "paint" requires multiple coats, each cured. These curing steps, of course, require the dental professional fashioning a pontic material using these older technologies to spend time, the time preparing, applying, curing and cleaning up the materials. More significantly, if there is any error whatsoever, since the systems previously employed are cured, it is hard or more typically impossible to recover, which requires the process to start over and is why this procedure is best done by an experienced professional. The material of the present disclosure typically never cures during the period of time the pontic material or retainer is in use and more typically never cures, giving an opportunity for an infinite number of corrections over any period of time to the shape to get it right.

Figure 3A:
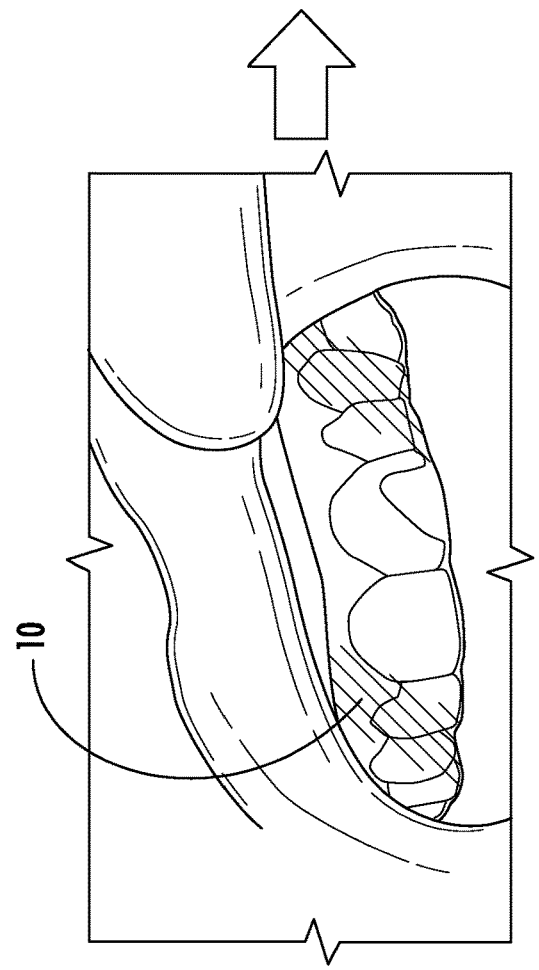
FIGS. 3A and 3B are perspective views of a chipped central incisor in a plastic aligner tray before and after application of the pontic material of the present application.
Figure 3B:
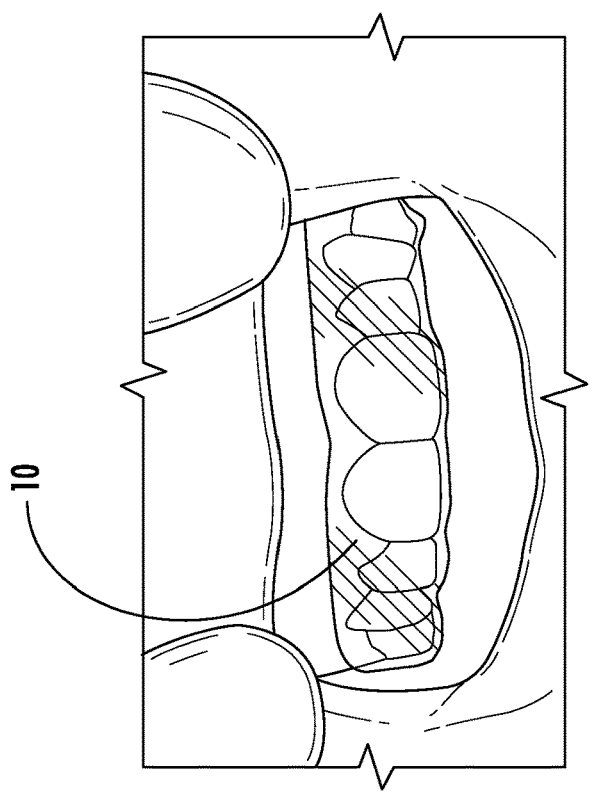
Figure 4B:
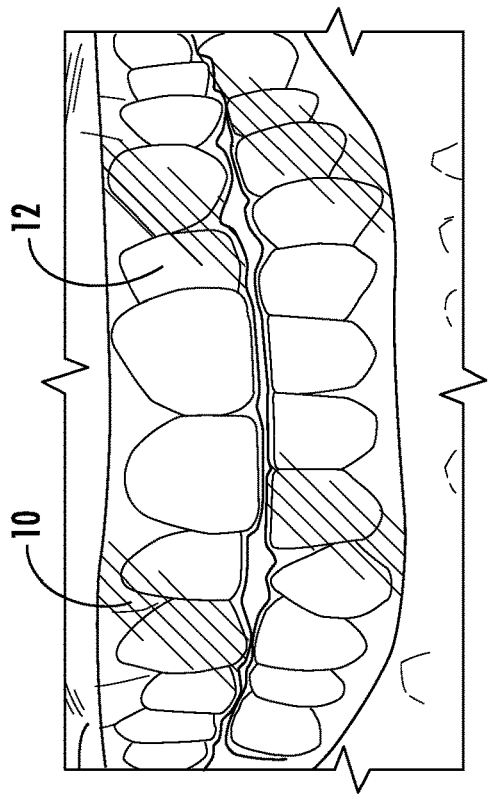
FIGS. 4A and 4B are before (FIG. 4A) and after (FIG. 4B) perspective views of how the pliability of the pontic material of the present disclosure allows for an automatic fit against an irregular gum line and chipped tooth and form a full tooth pontic within the aligner or retainer.
Figure 4A:
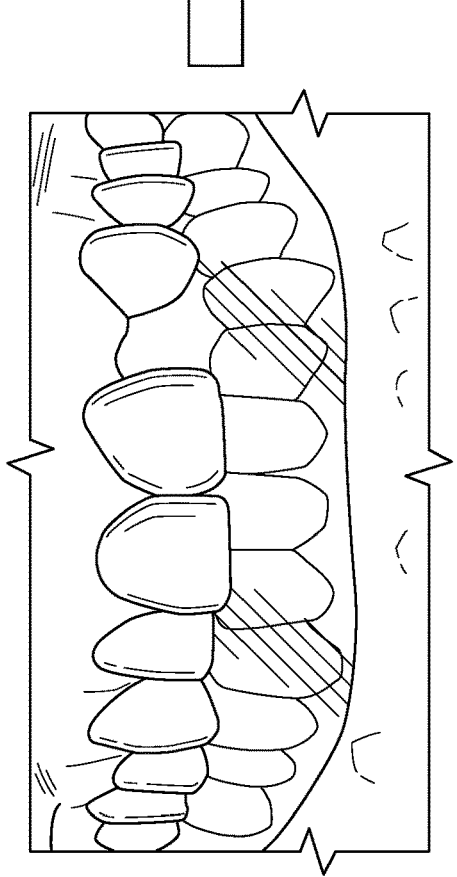

As shown in FIGS. 3A and 3B, the material of the present disclosure may form part of a chipped tooth shape within the interior of the aligner or retainer such that the tooth appears complete. FIG. 4A shows a clear retainer or aligner without material of the present disclosure used as false tooth material in the retainer or aligner. FIG. 4B shows the retainer or aligner with a material of the present disclosure forming a whole pontic tooth. The pontic materials of the present disclosure form a pleasing fit against the gum tissue or jagged edge of a chipped tooth essentially automatically when a patient places the aligner or retainer onto the teeth and the gum tissue or when the tooth presses into the pliable pontic material of the present disclosure due to it being uncured and pliable.

Uncured (uncrosslinked) silicone high consistency rubber (HCR) base material is a blend of one or more silicones with untreated and/or treated silica filler. The uncured (uncrosslinked) silicone high consistency rubber base material incorporates proprietary silicones, proprietary amounts of silicone or silica filler and proprietary silica filler material characteristics. In the industry, this information is kept a trade secret. An "uncured (uncrosslinked) silicone high consistency rubber base material" is a known category of silicone materials to chemists familiar with silicone polymers and/or silicone materials. Regarding the uncured (uncrosslinked) silicone HCR base material, many companies market uncured (uncrosslinked) silicone HCR base that could be used to prepare composites of the present disclosure, including but not limited to: Wacker ELASTOSIL® R PLUS 4000/50; Wacker ELASTOSIL® R 401/50 S; Wacker ELASTOSIL® R PLUS 4305/70; Wacker ELASTOSIL® R PLUS 4305/60; Wacker ELASTOSIL® R plus 4305/80; Wacker ELASTOSIL® R 401/80 S; Nusil MED-2174; Nusil MED-4174; Hoshine HS-5253 50; Dow Corning Silastic Q7-4535 Medical Grade ETR Elastomer; Dow Corning Silastic Q7-4550 Medical Grade ETR Elastomer; and Dow Corning Silastic Q7-4565 Medical Grade ETR Elastomer. Suitable base material may also be prepared with high viscosity polydimethylsiloxane, and/or vinyl-functionalized polydimethylsiloxane, and/or silanol-functionalized polydimethylsiloxane, and/or Si—H functional silicone combined with fumed silica or trimethylsilylated silica filler.

Regarding the metal oxide pigments used to obtain a color match of the silicone HCR base material to one of the VITA Classical Shade Guide colors, many companies market food grade metal oxide pigments that could be used to prepare the inventive pontic material, including but not limited to, white titanium dioxide, brown iron oxide blend, and yellow iron oxide from Sensient Pharmaceutical. In the case of the compositions of the present disclosure, it is significant that through the proper combination of pigments, it is possible to obtain an uncured pontic material in any of the 16 VITA shades. The VITA shades are one universal way to determine the color of a human tooth. The VITA classical A1-D4 shade guide serves to accurately determine tooth shade. The arrangement of the shades in the VITA classical family of shades is as follows: A1-A4 (reddish-brownish); B1-B4 (reddish-yellowish); C1-C4 (greyish shades); and D2-D4 (reddish-grey).

Additionally, a variety of immediate and time released flavorants such as mint flavorants, cinnamon or cinnamon flavorants, citrus flavors may also be employed. Time released flavorants are particularly effective when the pontic is used in connection with an orthodontic aligner tray or retainer, in particular in connection with a clear orthodontic aligner tray because each clear aligner tray is one of a series of clear orthodontic aligner trays where each tray is worn for many days and often about 2 weeks at a time. Having a fresher taste is advantageous. Additionally, the pontic material may include one or more preservatives to limited bacterial growth. In particular, the composition may include, but are not limited to any one or a plurality of the following: benzoic acid and salts thereof, sorbic acid and salts thereof, and parabens. Moreover, the pontic compositions of the present disclosure may optionally include an analgesic or antibacterial composition. Pontics are often used after extraction of a tooth or other mouth injury. Employing one or more analgesic and/or one or more antibacterial composition may help with the injury site pain and may help prevent infection at the site as well. The analgesic releases over time when blended with the pontic composition. The Analgesic would be drawn out of the pontic material over time by the saliva in the wearer's mouth. Exemplary analgesics that may be used alone or in combination in the pontic compositions of the present disclosure include: benzocaine; an NSAID such as ibuprofen; acetaminophen; and acetyl salicylic acid. Exemplary antibiotics that may be employed alone or in combination in pontic compositions of the present disclosure include, but are not limited to, erythromycin, clarithromycin and azithromycin.

According to an aspect of the present disclosure, the pontic material of the present disclosure was prepared by combining metal oxide pigment(s) with uncured (uncrosslinked) silicone HCR base (DOW CORNING. SILASTIC.ETR. Q7-4550) on a two-roll mill. Other mixing technologies that could be used include, but are not limited to, a sigma blade ("Z-blade") mixer and a double planetary mixer equipped with high viscosity blades or a SPEED-MIXER™, which is a double rotation of the mixing cup that is sometimes referred to as a dual asymmetric centrifuge. The combination of centrifugal forces acting on different levels in such a device enables very rapid mixing. Batches ranging up to 25 pounds were prepared using a two-roll mill. The following example illustrates the pigment compositions required to achieve inventive pontic material of VITA Shade D2 as established by visual comparison to a reference and by color mapping using camera input analyzed using SHADE-WAVE™ Dental Shade Matching Software (shadewave.com).

Example Pontic Material Vita Shade D2

| Example | % Q7-4550 | % titanium dioxide | % brown iron oxide blend | % yellow iron oxide |
|---|---|---|---|---|
| VITA Shade D2 | 99.964 | 0.0312 | 0.0012 | 0.0039 |

The amount of uncured, uncrosslinked silicone high consistency rubber base (Q7-4550, for example) typically ranges in amounts by weight of from about 99.90 to about 99.99 weight percent of the pontic composition, more typically from about 99.92 to about 99.98 weight percent of the pontic composition. The amount of titanium dioxide typically ranges from about 0.020 to about 0.055 weight percent, more typically from about 0.030 to about 0.045 weight percent of the pontic composition. The compositions of the present disclosure typically include one or a plurality of different iron oxides to adjust the color of the pontic to any appropriate VITA shade to match the person's other natural or artificial teeth color. For example, a first iron oxide and a second iron oxide may be employed. A third iron oxide or any number of subsequent iron oxides may be employed as well. Typically, the iron oxides employed are brown iron oxide and yellow iron oxide. The amount of brown iron oxide blend typically ranges from about 0.0005 to about 0.015, more typically from about 0.001 to about 0.010 weight percent of the pontic composition. The amount of yellow iron oxide typically ranges from about 0.002 to about 0.006, more typically from about 0.0030 to about 0.0050 weight percent of the pontic composition. The resulting pontic material may be rolled into sheets or extruded into rods or into pre-cut small pieces as possible modes of marketing. Red iron oxide pigment may also be used in combination with the above pigments to obtain a VITA Shade match. The materials are typically mixed together thoroughly at room temperature, a temperature of from about 65 degrees Fahrenheit to about 80 degrees Fahrenheit, but the temperature of the mixing is not presently believed to be critical.

An additional benefit of the pontic material of the present disclosure is the ability to adjust opacity from being completely opaque to translucent depending on the amount of titanium dioxide pigment and the thickness of the inventive pontic material. For example, the above example is opaque at a thickness of 3 mm, mostly opaque at a thickness of 2.5 mm, and somewhat translucent at a thickness of 2 mm or less. Natural teeth often progress from opaque to somewhat translucent as one progresses from the cervical to the incisal edge. The inventive pontic material allows one to mimic this behavior by varying the amount of titanium dioxide pigment in the material and/or the thickness of the material once placed into the aligner or retainer.

What is claimed is:

1. A pontic material comprising a combination of an uncured, uncrosslinked silicone rubber base material and at least one metal oxide pigment mixed therein;
   wherein the pontic material is never cured;
   wherein the uncured, uncrosslinked silicone rubber base material makes up about 99.90 to about 99.99 weight percent of the pontic material;
   wherein the at least one metal oxide pigment comprises titanium dioxide in an amount of about 0.06 weight percent of the pontic material or less; and
   wherein the pontic material is opaque at a thickness of 3 mm, mostly opaque at a thickness of 2.5 mm, and at least partially translucent at a thickness of 2 mm or less.

2. The pontic material of claim 1, wherein the pontic material is pliable with human fingers without the use of tools and wherein the pontic material is free of any adhesive component.

3. The pontic material of claim 1, wherein the at least one metal oxide pigment further comprises a metal oxide pigment chosen from a group consisting of brown iron oxide blend, yellow iron oxide, and combinations thereof and wherein the pontic material is pliable with human fingers without the use of tools before, during and after use as a pontic within a user's mouth.

4. The pontic material of claim 3, wherein the at least one metal oxide pigment is a plurality of metal oxide pigments and the pontic material consists of the combination of the uncured, uncrosslinked silicone rubber base material and the plurality of metal oxide pigments mixed therein such that the pontic material has a color of a human tooth and wherein the pontic material is permanently pliable.

5. The pontic material of claim 1, wherein the at least one metal oxide pigment further comprises a metal oxide pigment chosen from a group consisting of brown iron oxide blend, yellow iron oxide, and combinations thereof.

6. The pontic material of claim 1, wherein the pontic material consists essentially of the uncured, uncrosslinked silicone rubber base material and the at least one metal oxide pigment mixed therein.

7. The pontic material of claim 1, wherein the pontic material consists of the uncured, uncrosslinked silicone rubber base material and the at least one metal oxide pigment mixed therein.

8. The pontic material of claim 1, wherein the at least one metal oxide pigment is a blend of the titanium dioxide, a brown iron oxide blend, a yellow iron oxide, and combinations thereof.

9. The pontic material of claim 1, wherein the pontic material is configured to be positioned within an interior of an aligner or retainer such that the pontic material is engaged with an inner surface of the aligner or retainer.

10. The pontic material of claim 1, wherein the at least one metal oxide pigment is a single metal oxide pigment that is the titanium dioxide and the titanium dioxide is present in an amount of from about 0.020 to about 0.055 weight percent of the pontic material.

11. The pontic material of claim 1, wherein the at least one metal oxide pigment further comprises a blend of iron oxide in an amount of from about 0.0025 to about 0.0075 weight percent of the pontic material.

12. The pontic material of claim 1, wherein the at least one metal oxide pigment further comprises a blend of a first iron oxide in an amount of from about 0.0005% to about 0.015% by weight of the pontic material and a second iron oxide in an amount from about 0.002% to about 0.0075% by weight of the pontic material.

13. The pontic material of claim 1, wherein the pontic material is free of an adhesive and the pontic material is an extruded pontic material.

14. The pontic material of claim 1, wherein the at least one metal oxide pigment comprises from about 0.020 to about 0.055 weight percent of the titanium dioxide, a first iron oxide in an amount of about 0.01 or less weight percent of the pontic material, a second iron oxide in an amount of about 0.003 weight percent of the pontic material, and 0.001 percent by weight brown iron oxide.

15. A kit comprising:
a pontic material that forms a finger pliable pontic that is free of a curing catalyst and the finger pliable pontic is uncured before use as a pontic within a wearer's mouth, during use within a wearer's mouth and after use within a wearer's mouth; and wherein the pontic material used to form the finger pliable pontic consists of a combination of an uncured, uncrosslinked silicone rubber base material in an amount of 99.90 to about 99.99 weight percent of the pontic material and at least one metal oxide pigment mixed therein in an amount of up to about 0.06 weight percent of the pontic material; and
a plastic orthodontic aligner or retainer.

16. The kit of claim 15 further comprising an elongated shaping tool configured to shape the pontic material into the pontic at a tooth location of the plastic orthodontic aligner or retainer.

17. The kit of claim 16, wherein the at least one metal oxide pigment is a blend of titanium dioxide, a brown iron oxide blend, a yellow iron oxide, and combinations thereof and wherein the pontic material is permanently pliable; and
wherein the pontic material is opaque at a thickness of 3 mm and translucent under a thickness of about 2.5 mm about 2.5 mm.

18. The kit of claim 15, wherein the pontic material is uncured and the pontic material is free of an adhesive.

19. A method of forming a pontic comprising the steps of:
placing a pontic material into contact with a teeth facing surface of a plastic orthodontic aligner or retainer;
wherein the pontic material comprises a combination of an uncured, uncrosslinked silicone rubber base material and a metal oxide pigment mixed therein and wherein the uncured, uncrosslinked silicone rubber base material makes up about 99.90 to about 99.99 weight percent of the pontic material;
wherein the metal oxide pigment comprises titanium dioxide in an amount of about 0.06 weight percent of the pontic material or less; and
wherein the pontic material is opaque at a thickness of 3 mm, mostly opaque at a thickness of 2.5 mm, and at least partially translucent at a thickness of 2 mm or less; and
forming a shape of an entire tooth or a portion of a tooth from the pontic material such that when the plastic orthodontic aligner or retainer is worn the pontic mimics the existence of the entire tooth or a portion of a tooth; and
wherein the pontic material never cures:
before the pontic material is formed into the shape of an entire tooth or a portion of a tooth;
while the pontic material is formed into the shape of an entire tooth or a portion of a tooth; or
after the pontic material is formed into the shape of an entire tooth or a portion of a tooth.

20. The method of forming a pontic of claim 19, wherein the step of forming of the pontic material is done using a force applicator chosen from the group consisting of: a human's fingers; and an elongated molding tool to mold the pontic material into the shape of the entire tooth or the portion of the tooth;
wherein the metal oxide pigment is a blend of the titanium dioxide, a first iron oxide blend, and a second iron oxide; and
wherein the pontic material is permanently uncured and is free of a curing catalyst.

* * * * *